United States Patent [19]

Krespan et al.

[11] Patent Number: 5,336,801
[45] Date of Patent: Aug. 9, 1994

[54] PROCESSES FOR THE PREPARATION OF 2,2,3,3-TETRAFLUOROPROPIONATE SALTS AND DERIVATIVES THEREOF

[75] Inventors: Carl G. Krespan, Wilmington, Del.; Allen C. Sievert, Elkton, Md.

[73] Assignee: E. I. Du Pont de Nemours and Company, Wilmington, Del.

[21] Appl. No.: 945,074

[22] Filed: Sep. 15, 1992

[51] Int. Cl.$^5$ .............................................. C07C 69/63
[52] U.S. Cl. .................................................. 560/227
[58] Field of Search ........................ 560/277; 562/605

[56] References Cited

U.S. PATENT DOCUMENTS 2,802,028  8/1957  England ................................ 562/605
4,808,651  2/1989  Blickle et al. ......................... 524/366

FOREIGN PATENT DOCUMENTS 54-009171  4/1979  Japan .

OTHER PUBLICATIONS

England, et al., *Org. Synth.*, 1960, 40, 11.

*Primary Examiner*—José G. Dees
*Assistant Examiner*—Joseph M. Conrad
*Attorney, Agent, or Firm*—Susan Borden Evans

[57] ABSTRACT

This invention relates to chemical processes for preparing tetrafluoropropionate salts and selected derivatives thereof.

21 Claims, No Drawings

PROCESSES FOR THE PREPARATION OF 2,2,3,3-TETRAFLUOROPROPIONATE SALTS AND DERIVATIVES THEREOF

BACKGROUND OF THE INVENTION

1. Field of the Invention

This invention relates to chemical processes for preparing tetrafluoropropionate salts and selected derivatives thereof.

2. Background

The preparation of polyfluorocarboxylic compounds, including tetrafluoropropionates, by the reaction of water and a metal cyanide with a fluoroolefin, including tetrafluoroethylene, has been disclosed in U.S. Pat. No. 2,802,020. The presence in the reaction mixture of a water-soluble inert organic liquid reaction medium is also disclosed therein. The reference further states that such water-soluble inert organic liquid reaction media are preferably free of alcoholic hydroxyls.

U.S. Pat. No. 4,808,651, relating to solutions of fluoropolymers, discloses preparation of several fluorinated solvents, including the $\alpha,\psi$-dihydroperfluoroalkane $CHF_2(CF_2)_nCHF_2$ wherein n is 6, by Kolbe electrolysis of $\psi$-hydrooctafluorovaleric acid in 2:1 water:methanol. HFC-338pcc is disclosed by generic formula.

SUMMARY OF THE INVENTION

The present invention provides a process for preparing 2,2,3,3-tetrafluoropropionate salt comprising reacting cyanide salt and water with tetrafluoroethylene (TFE) in the presence of an alcohol. Use of an alcohol in the present process for preparing 2,2,3,3-tetrafluoropropionate salt results in higher yields and provides a desirable medium for subsequent electrolysis of said salt to 1,1,2,2,3,3,4,4-octafluorobutane (hereinafter referred to as "HFC-338pcc"). The process can be extended to provide 2,2,3,3-tetrafluoropropionic acid and $C_1$-$C_4$ alkyl esters of 2,2,3,3-tetrafluoropropionic acid from the propionate salts. The process can be further extended to provide HFC-338pcc and azeotropes thereof with alcohols by electrolysis of the propionate salt, acids or esters in the presence of water and water-miscible organic liquid.

Also provided are processes wherein the unpurified reaction mixture of the TFE/water/alcohol reaction or $C_1$-$C_4$ alkyl 2,2,3,3-tetrapropionate ester, is converted to HFC-338pcc by Kolbe electrolysis in the presence of water and optionally a water-miscible organic liquid.

DETAILS OF THE INVENTION

Cyanide salts useful for preparing 2,2,3,3-tetrafluoropropionate salts according to the process of this invention are selected from the group consisting of MCN wherein M is an alkali metal having an atomic number greater or equal to 11, $Ca(CN)_2$, $Mg(CN)_2$ and $R_4NCN$, wherein R is $C_1$-$C_4$ alkyl. Preferred cyanide salts are selected from the group consisting of NaCN, KCN, and $R_4NCN$ where R is $C_1$-$C_4$ alkyl.

The reactions are carried out in the presence of mono- or polyhydric alcohols which are preferably miscible with water and are solvents in the reaction medium. Preferred alcohols, which may be primary, secondary or tertiary, are selected from the group consisting of monohydric alcohols ROH where R is $C_1$-$C_8$alkyl; ethylene glycol; propylene glycol; 1,4-butanediol; and mixtures thereof. Monohydric alcohols ROH where R is $C_1$-$C_4$ alkyl are more preferred. Most preferred are methanol and ethanol. The use of alcohols promotes higher yields of 2,2,3,3-tetrafluoropropionate salt, increases reaction rates and provides a desirable medium for subsequent electrolysis to HFC-338pcc.

Additional water-miscible organic compounds including, for example, acetonitrile, propionitrile, dimethyl formamide, dimethyl acetamide, or tetrahydrofuran may also be present. Such compounds increase the solubility of TFE in the reaction medium.

The molar ratio of water to cyanide salt should be at least 2:1 and may be as high as 50:1. Preferably the ratio is about 4:1 to 20:1. The alcohols are added to the water to provide alcohol/water mixtures containing about 5 to about 95% by volume of water. Preferably the water content is about 10 to about 75%, most preferably about 20 to about 60% by volume.

The amount of tetrafluoroethylene employed is not critical. However an amount of TFE within about 10 mol % of the molar amount is desirable to minimize unreacted cyanide.

The process for making the 2,2,3,3-tetrafluoropropionate salt can be carried out at temperatures in the range of about 15° to about 125° C., preferably about 40° to about 100° C. Reaction pressure may be in the range of about 15 to about 1000 psi (103 kPa to 6900 kPa), preferably about 50 to about 300 psi (345 kPa to 2070 kPa). Reaction conditions should normally be continued for sufficient time after addition of TFE is complete to insure complete reaction of the TFE and to optimize conversion of intermediates to the propionate salts.

2,2,3,3-Tetrafluoropropionic acid (hereinafter referred to as "TFPA") may be liberated from its salt by hot venting or refluxing the reaction mixture to remove the ammonia by-product of the reaction forming the propionate salt, distilling to remove alcohol, then treating the residual reaction mixture with a strong mineral acid such as hydrochloric acid phosphoric acid or sulfuric acid, preferably sulfuric acid. TFPA may be isolated by conventional methods such as direct distillation from the acidified solution, or by extraction from the acidified solution such as by using solvents selected from the group consisting of ethers and halogenated compounds, followed by distillation. Representative ethers include diethyl ether, tetrahydrofuran, 1,2-dimethoxyethane, diisopropyl ether and dioxane. Representative halogenated compounds include dichloromethane and chloroform. TFPA may also be isolated from the crude reaction mixture by distilling away all volatile components to leave a solid cake; the cake is then treated with a strong mineral acid and TFPA is distilled from the resulting mixture (b.p. 66°–67° C. at 50 mm (6.7 kPa)).

The TFPA can be converted to $C_1$-$C_4$ alkyl ester by acidifying the reaction mixture containing the propionate salt in the presence of a $C_1$-$C_4$ alcohol, preferably methanol or ethanol, then isolating the esters by distillation as mixtures or azeotropes with the alcohol present in the reaction mixture. The mixtures comprise about 10 to about 60% by weight of the propionate ester and about 90 to about 40% by weight of the alcohol. The azeotrope of methyl 2,2,3,3-tetrafluoropropionate and methanol so prepared boils at about 63.0°–64.5° C. and contains about 46–48% by weight of propionate ester and about 52–54% by weight of methanol.

The 2,2,3,3-tetrafluoropropionate salts, 2,2,3,3-tetrafluoropropionic acid (TFPA), $C_1$-$C_4$ alkyl esters thereof, and azeotropes of these esters with the respective alcohols, may be converted to HFC-338pcc by electrolysis in conventional Kolbe electrolysis equipment, in the presence of water and a water-miscible organic liquid.

The unpurified reaction mixture from the reaction of TFE with cyanide salt is a particularly suitable source of the 2,2,3,3-tetrafluoropropionate salt for electrolytic preparation of HFC-338pcc; prior hot venting or refluxing to remove residual ammonia by-product at the end of the propionate salt-forming reaction is desirable but not essential. Residual compounds such as alcohol, water and water-miscible organic liquids remaining in the salt-forming reaction mixture are beneficial in the electrolysis, and reaction by-products present have proved not to be detrimental in the electrolysis.

The derivative TFPA, $C_1$-$C_4$ alkyl esters, or azeotropes of the ester are also a desirable starting material for the electrolytic production of HFC-338pcc. With TFPA, esters and their respective azeotropes, addition of a base may be necessary at the start of electrolysis to at least partly convert these materials to electrolytes.

The Kolbe electrolysis may be operated in batch, semi-continuous or continuous mode. In the latter modes, a conventional electrolysis cell is charged with electrolyte (propionate salt, acid or ester) and, as electrolysis proceeds, additional propionate salt, TFPA or ester is fed to the cell as required to maintain steady state electrolysis. A Kolbe batch electrolysis procedure wherein 5-hydrooctafluoro-1-valeric acid is converted to 1,8-dihydrohexadecafluorooctane is disclosed in U.S. Pat. No. 4,808,651 at column 7, line 65 to column 9, line 25, which is herein incorporated by reference. The electrolysis process of the invention may also be carried out in a flow electrolysis cell such as the MP cell available from Electrocell AB (Sweden), or the FM01-LC cell available from ICI (America), operated either unpartitioned or partitioned with a membrane. The flow cells may be operated in batch or continuous modes. Cathodes for the present process may be of Pt, Ni, Fe, steel, Cu or other conducting materials. Anodes are preferably Pt or Pt-coated.

The addition of electrolytes other than those employed as reactants or formed as by-products in the reaction, such as, for example, NaF, $Na_2SO_4$ or $(NH_4)_2SO_4$ may be beneficial to HFC-338pcc yields or cell performance, provided said other electrolytes are chemically inert under process conditions.

In the electrolytic production of HFC-338pcc, suitable water-miscible organic liquids include, for example, $C_1$-$C_4$ monohydric alcohols, acetonitrile, propionitrile, ethylene glycol, propylene glycol, dimethyl formamide or mixtures thereof; methanol, ethanol or mixtures of methanol and acetonitrile are preferred. The alcohol can come from the propionate salt forming reaction mixture, or from use of a propionate ester/alcohol azeotrope, or can be added when the electrolysis is to be carried out. The primary purpose of the water-miscible organic liquid is to insure the solubility of the reactants in the electrolysis medium.

Suitable bases for use when TFPA is the electrolysis starting material include sodium hydroxide, potassium hydroxide or ammonium hydroxide; sodium hydroxide is preferred. Operable water/organic liquid mixtures may contain about 15% to about 95% by volume of water, preferably about 30% to about 85%, most preferably about 40% to about 75% by volume. The number of g equivalents of base added per mole of TFPA in the electrolysis may be in the range of about 0.01 to about 1.5, preferably about 0.1 to about 1.0. TFPA concentration in the electrolysis solution should be at least about 0.5 mole/liter, preferably at least about 1.0 mole/liter, most preferably at least about 2.0 moles/liter.

The solution should have a pH of less than 7, preferably less than about 6. Cell temperature is not critical, but operation at maximum temperatures of about 20° to about 60° C. is satisfactory, temperatures below about 50° C. being preferred. In batch operation it is desirable to cool the solution to about 0° to 5° C. prior to electrolysis to compensate for exothermic temperature rise during electrolysis. Stirring of the solution during electrolysis is desirable. HFC-338pcc product, usually in the form of an azeotrope with alcohol, distils during electrolysis and is condensed outside the electrolysis cell.

The propionate salts, TFPA and propionate esters are all useful for making HFC-338pcc.

HFC-338pcc and its azeotropes with alcohols are useful as cleaning agents, especially for cleaning the surfaces of electronic components. The current solvent of choice for cleaning surfaces, 1,1,2-trichloro-1,2,2-trifluoroethane (hereinafter referred to as "CFC-113"), contains chlorine and has been implicated in the depletion of the stratospheric ozone layer. Thus a major need exists for solvents like HFC-338pcc and its azeotropes which are free of chlorine and have no adverse effect on the ozone layer.

EXAMPLE 1

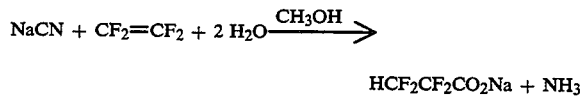

$HCF_2CF_2CO_2Na + NH_3$

A 1-L stirred autoclave was charged with 98.0 g (2.0 mol) of sodium cyanide, 100 mL (100 g) of water, and 400 mL (316 g) of methanol and stirred at 40° C. while 50 g (0.50 mol) of tetrafluoroethylene was added in portions to maintain 75–105 psi (618 kPa to 825 kPa) pressure. The temperature was raised to 80° C. to increase the reaction rate, and tetrafluoroethylene was added continuously at 66 g/hr for 1.5 hr while the pressure rose slowly to 105 psi (618 kPa). The addition of tetrafluoroethylene was continued intermittently at 80° C. until a total of 200 g (2.0 mol) had been added. The stirring was continued at 80° C. for 2 hr while the pressure fell from 100 psi (791 kPa) to 72 psi (598 kPa). The dark orange liquid product, 676 g, was shown by $^1H$ and $^{19}F$ NMR analysis to contain 279.4 g (83% conv.) of $HCF_2CF_2CO_2Na$ with a combined 6% of two intermediate products present, along with 3.1 g $HCF_2CO_2Na$.

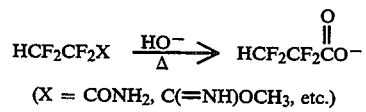

(X = $CONH_2$, C(=NH)$OCH_3$, etc.)

A 100-mL aliquot of the above reaction mixture was refluxed for 6 hr, during which time the temperature in the pot rose from 59° C. to 73° C. and 8 mL of liquid (mainly $NH_3$) collected in a −80° C. trap. Analysis of the solution by $^{19}F$ NMR showed the two major by-products (amide and a precursor) were largely converted to $HCF_2CF_2CO_2Na$ while the small amount (~1%) of $HCF_2CO_2Na$ remained unchanged.

EXAMPLES 2-6

NaCN/CF$_2$=CF$_2$/H$_2$O/CH$_3$OH Reactions

The reaction conditions of Example 1 were varied. The conditions and the results are shown in Table 1.

TABLE 1

| Ex. | NaCN mol | TFE psi(kPa) | H$_2$O CH$_3$OH$^a$ (% by vol) | Temp. °C. | Time hr | STFP$^b$ % yield$^e$ | Int.$^c$ % yield$^e$ | SDF$^d$ (mol) |
| --- | --- | --- | --- | --- | --- | --- | --- | --- |
| 2 | 0.50 | 150(1,136) | 20 | 100 | 1.5 | 88 | 12 | 0.13 |
| 3 | 2.50$^f$ | 150(1,136) | 50 | 100 | 8.0 | 91 | — | 0.45 |
| 4 | 1.50 | 100(791) | 35 | 70 | 4.5 | 85 | 2 | 0.03 |
| 5 | 0.50 | 50(446) | 20 | 40 | 8.0 | 52 | 16$^g$ | <0.01 |
| 6 | 1.50 | 100(791) | 35 | 70 | 7.5 | 96 | 3$^g$ | 0.08 |

$^a$Volume H$_2$O + CH$_3$OH = 500 mL
$^b$STFP = Sodium 2,2,3,3-Tetrafluoropropionate
$^c$Int. = Intermediates
$^d$SDF = Sodium Difluoroacetate
$^e$% yield on NaCN
$^f$Cyanide ion by ion chromatography was < 1 mg/mL solution
$^g$Completely converted to HCF$_2$CF$_2$CO$_2$Na after reflux for 6 h

EXAMPLE 7

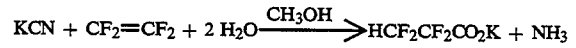

A 1-L stainless steel autoclave was charged with 97.7 g (1.5 mol) of potassium cyanide, 325 mL of methanol and 175 mL of water, then stirred at 77°–80° C. while 150 g (1.50 mol) of tetrafluoroethylene was pressured in over a period of 2 hr, 20 min. Pressure rose to 126 psi (969 kPa) during this period, then fell to 39 psi (370 kPa) while stirring was continued at 80° C. for an additional two hours. Product solution, 637.6 g, was shown by $^{19}$F NMR to contain 219.8 g (80%) of potassium 2,2,3,3-tetrafluoropropionate along with 1% of tetrafluoropropionate precursor and 4.1 g of potassium difluoroacetate.

EXAMPLE 8

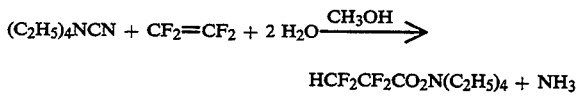

A reaction similar to that above was carried out at 80° C. with 67.6 g (0.43 mol) of tetraethylammonium cyanide and 45 g (0.45 mol) of tetrafluoroethylene to give 525.1 g of clear solution. Analysis by $^{19}$F NMR indicated the presence of 94.9 g (80%) of tetraethylammonium 2,2,3,3-tetrafluoropropionate and 8% of intermediates to the tetrafluoropropionate, but no by-product difluoroacetate salt.

These intermediates were shown by NMR analysis to be completely converted to tetrafluoropropionate salt by refluxing the solution at 1 atm. for 6 hr, during which time most of the ammonia present was driven off.

EXAMPLE 9

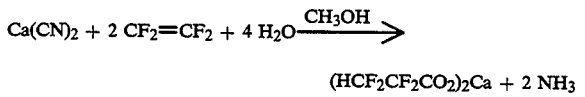

A 1-L autoclave charged with 69.1 g (0.75 mol) of calcium cyanide, 325 mL of methanol, and 175 mL of water was stirred at 80° C. while 61.6 g (0.62 mol) of tetrafluoroethylene was pressured in over a 5.5 hr. period. The reaction was then run at 80° C. for another 4 hr. The dark product, 515.4 g, contained finely divided solid that was removed by centrifugation prior to analysis. $^{19}$F NMR showed the presence of 54.7 g (54% based on tetrafluoroethylene) of calcium 2,2,3,3-tetrafluoropropionate, with 13.7 g of calcium difluoroacetate as substantially the only fluorinated by-product.

EXAMPLE 10

Ethanol as Cosolvent

A mixture of 49.0 g (1.0 mol) of sodium cyanide, 100 mL of water, and 400 mL of absolute ethanol was stirred at 80° C. in a 1-L autoclave while 50.6 g (0.506 mol) of tetrafluoroethylene was added at 75-100 psi (618-790 kPa). Stirring was then continued at 80° C. for 2 hr. The product was 489.2 g of nearly colorless liquid shown by $^{19}$F NMR to contain 70.2 g (42% based on NaCN; 83% based on tetrafluoroethylene) of sodium 2,2,3, 3-tetrafluoropropionate, along with small amounts of two intermediates and 0.3 g of sodium difluoroacetate.

EXAMPLE 11 tert-Butanol as Cosolvent

Reaction of 73.5 g (1.5 mol) of sodium cyanide, 325 mL of tert-butanol, 175 mL of water, and 151.8 g (1.52 mol) of tetrafluoroethylene was carried out at 80° C. in a 1-L autoclave. $^{19}$F NMR analysis of the reaction mixture, 615.6 g, showed 218.5 g (87%) of sodium 2,2,3,3-tetrafluoropropionate and 5.4 g of sodium difluoroacetate to be present.

EXAMPLE 12

Isolation of HCF$_2$CF$_2$CO$_2$H From Dry Salt

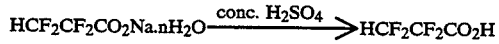

The crude product from example 11 was distilled at 1 atm. until the head temperature reached 90° C., then warmed at 70° C. (<1 mm) to obtain 233.6 g of dry solid. The solid cake was broken up and treated with 250 mL of conc. sulfuric acid. The resulting mixture was stirred at 100° C. until dissolution of the solid product was complete, then distilled under vacuum to afford 195.5 g colorless liquid, bp 66°–67° C. (50 mm).

GC exhibited a single peak, while NMR analysis showed the distillate to be anhydrous 2,2,3,3-tetrafluoropropionic acid with 1.2% of difluoroacetic acid as the only impurity. The calculated amounts based on analysis of the crude salt solution were 189.9 g of 2,2,3,3-tetrafluoropropionic acid and 4.4 g of difluoroacetic acid.

EXAMPLE 13 n-Butanol as Component of a Ternary Solvent

A 1-L autoclave charged with 49.0 g (1.0 mol) of sodium cyanide, 100 mL of water, 300 mL of n-butanol, and 100 mL of acetonitrile was stirred at 80° C. while 100 g (1.0 mol) of tetrafluoroethylene was injected continuously over a 1.5-hr period. Reaction was continued for another 4 hr, after which time 540.1 g of clear liquid product was obtained. Analysis by $^{19}$F NMR indicated it to contain 148.3 g (88%) of sodium 2,2,3,3-tetrafluoropropionate and 1.3 g of sodium difluoroacetate.

EXAMPLE 14

Isolation of $HCF_2CF_2CO_2H$ by Liquid-Liquid Extraction with $CH_2CCl_2$

A sample of crude product from Example 6, after reflux for 6 hr, was indicated by NMR analysis to contain 1.254 mol of $HCF_2CF_2CO_2Na$ and 0.047 mol of $HCF_2CO_2Na$ impurity. This solution was diluted with 300 mL of water and distilled at 1 atm. until methanol had been removed (head temp.=98° C). A cold solution of 120 mL of concentrated sulfuric acid in 400 mL of water was added, and the resulting clear solution was extracted continuously with methylene chloride until only traces of product were being removed. The extracts were fractionated in a spinning band column to give, after removal of solvent, 6.9 g of foreshot, bp 27°-64.5° C. (50 mm), followed by 167.9 g of nearly anhydrous 2,2,3,3-tetrafluoropropionic acid, bp 64.5°-66.4° C. (50 mm), identified by $^1$H and $^{19}$F NMR. The calculated amount of 2,2,3, 3-tetrafluoropropionic acid available based on analysis of the crude salt solution was 183.1 g. NMR also indicated the presence of 2.5 mol-% of difluoroacetic acid.

EXAMPLE 15

Isolation of $HCF_2CF_2CO_2H$ by Extraction with Diethyl Ether

Reaction of a solution of 98.0 g (2.0 mol) of sodium cyanide in 325 mL of methanol and 175 mL of water with excess tetrafluoroethylene was done at ca 80°-90° C. in a stirred autoclave. Analysis of the reaction mixture, 678.8 g, by $^{19}$F NMR indicated the presence of 279.2 g (83.1%) of $HCF_2CF_2CO_2Na$ and 12.1 g (0.10 mol) of by-product $HCF_2CO_2Na$. This crude product was combined with 300 mL of water and distilled until the head temperature reached 95° C. The residual aqueous solution was cooled and treated with 106.6 g (1.05 mol) of 96.5% $H_2SO_4$. The resulting solution was cooled to 25° C. and extracted with 500 mL, then 2×200 mL of diethyl ether; the third extract was shown by GC to contain only traces of $HCF_2CF_2CO_2H$. The combined ether extracts were washed with 500 mL of water, and the aqueous layer was back-extracted with another 200 mL of ether. The total combined ether solutions were mixed with 54 mL of water and distilled to give recovered ether, then water, bp 35°-37.8° C. (50 mm, 6.7 kPa), and finally 259.4 g of product, b.p. 48°-68° C. (50 mm, 6.7 kPa). Analysis by NMR indicated the presence of 234.4 g (97% recovery) of $HCF_2CF_2CO_2H$ and 9.8 g (100% recovery) of $HCF_2CO_2H$ along with a small amount of water.

EXAMPLE 16

Separation of $HCF_2CF_2CO_2H$ by Distillation from Acidified Aqueous Reaction Mixture A reaction of 98.0 g (2.0 mol) of sodium cyanide and 200 g (2.0 mol) of tetrafluoroethylene was carried out at 75°-80° C. in a mixture of 325 mL of methanol and 175 mL of water as solvent. The product solution, 699.0 g, was indicated by NMR analysis to contain 288.7 g (86%) of $HCF_2CF_2CO_2Na$ and 5.2 g of $HCF_2CO_2Na$. Distillation to remove ammonia and methanol (head temperature=95° C.) was followed by treatment with 106.6 g (1.05 mol) of 96.5% $H_2SO_4$. Further distillation gave 214.1 g product as a fraction, bp 65°-67° C. (50 mm, 6.7 kPa). Analysis by NMR indicated the distillate to contain 214.1 g (84% recovery) of $HCF_2CF_2CO_2H$ and 4.2 g of $HCF_2CO_2H$ with little water present.

EXAMPLE 17

Separation of $CHF_2CF_2CO_2H$ as Methyl Ester and Sodium Ion as $Na_2SO_4$

Crude product from Example 4 was filtered and refluxed for 6 hr to remove ammonia and complete conversion of intermediates to $HCF_2CF_2CO_2Na$. The cooled mixture was then stirred while 76.1 g (0.75 mol) of 96.6% $H_2SO_4$ was added slowly, keeping the temperature below 30° C. The mixture was filtered and the filter cake was rinsed with 2×50, 100, then 50 mL of methanol. The dried, white, granular solid, 87.0 g, was shown by X-ray analysis to be $Na_2SO_4$. The filtrate deposited another 2.3 g on standing for a total of 89.3 g of $Na_2SO_4$.

Distillation of the combined filtrates afforded 0.3 g of binary mixture, bp 63.4°-68.0° C. with the bulk of the azeotrope bp 63.4°-64.1° C. Analysis of the bp 63.4°-64.1° C. fraction by $^1$H and $^{19}$F NMR and GC indicated 53.3 wt-% $CH_3OH$ and 46.7 wt-% $HCF_2CF_2CO_2CH_3$ to be present with only minor amounts of $HCF_2CF_2CO_2H$ and $HCF_2CO_2CH_3$ detected.

Further distillation gave 61.4 g of water, bp 38.1°-38.5° C. (50-mm, 6.7 kPa), and only 5.6 g of crude $HCF_2CF_2CO_2H$ hydrate, bp 41°-59° C. (50 mm, 6.7 kPa). The residue of nearly dry crude salts weighed 18.7 g.

If desired, the azeotrope, bp 64.1° C., can be broken by distillation with a third component. For example, distillation of the mixture with n-pentane removes methanol as azeotrope with n-pentane, bp 29.7°-30.2° C.

EXAMPLE 18

Use of Phosphoric Acid for Separation of $HCF_2CF_2CO_2CH_3$

Reaction of 122.0 g of NaCN, 0.8 g of NaOH, and 250 g of tetrafluoroethylene in 405 mL of methanol and 220 mL of water was carried out at 80° C. in a stirred autoclave to give 863.5 g of solution containing 415.4 g (2.47 mol) of $HCF_2CF_2CO_2Na$. This mixture was refluxed for 6 hr to volatilize the bulk of ammonia present, and an 83 g aliquot containing 42 g (0.25 mol) of $HCF_2CF_2CO_2Na$ was taken. This aliquot was stirred while 57.6 g (0.50 mol) of 85% $H_3PO_4$ was added dropwise, and the resulting mixture was stirred overnight. Two layers were present, including a lower layer which contained some $NaH_2PO_4$ as a precipitate. The mixture was stirred at reflux for 10 min., after which time two clear layers were present. On standing, salts crystallized from the lower layer. The two liquid layers were separated in a separatory funnel. The upper layer, 31.6 g, was shown by GC analysis to be composed of about 90.5% $HCF_2CF_2CO_2CH_3$ and a small proportion of $HCF_2CF_2CO_2H$, for a recovery of 28.6 g (72%). The other major component was methanol.

EXAMPLE 19

Preparation of 1,1,2,2,3,3,4,4-Octafluorobutane (HFC-338pcc) by Kolbe Electrolysis of the Reaction of TFE with Sodium Cyanide The liquid reaction mixture (25 ml) from the reaction of TFE with sodium cyanide from Example 1, which was 3.26 M with respect to TFPA, was diluted with water (50 mL). The pH of the solution was adjusted to 5.3 with aqueous HCl. The solution was poured into an electrolysis cell and cooled to 10° C. A current of 4 amperes (13.7–14.3 volts) was maintained until 15,000 coulombs of electricity were passed; during this time the temperature in the cell rose to 39° C. The final pH of the cell contents was 10.0. A total of 4.43 g of liquid was obtained in a dry ice trap attached to the exit side of the condenser on the cell. Analysis of the trap material by GC is shown the table.

| Component | GC Area % |
|---|---|
| $CHF_2CF_3$ | 0.4 |
| $CH_2FCHF_2$ | 1.6 |
| $CHF_2CClF_2$ | 8.8 |
| $CH_3OH$ | 5.3 |
| HFC-338 pcc | 77.8 |
| $CHF_2CF_2OCH_3$ | 4.2 |
| unidentified | 0.5 |
| $C_4HF_7$(probable) | 0.5 |
| $C_6HF_{11}$(probable) | 0.1 |

The yield of $CHF_2(CF_2)_2CHF_2$ (HFC-338pcc) measured by gas chromatography was 40% based on the TFPA charged to the cell. The conversion of TFPA based on $^{19}F$ NMR was 69%.

EXAMPLE 20

Conversion of 2,2,3,3-Tetrafluoropropionic Acid (TFPA) to HFC-338pcc

A solution of TFPA was prepared by mixing methanol (40 ml), water (40 ml), TFPA (36.0 g of 90.3 weight % acid, 0.223 mole), and sodium hydroxide (4.8 g, 0.120 mole) into the Kolbe electrolysis cell of Example 19. The initial pH was about 1.3. The solution was cooled to about 2° C. and then electrolyzed at a current of 4 amp; the cell voltage was in the range of 13–14 v. The cell temperature rose rapidly to 25° C. and continued to rise during the electrolysis to about 41° C. at the end of electrolysis The products in the dry ice trap were collected periodically. After 28,500 coulombs had been passed, the electrolysis was stopped. The total yield of HFC-338pcc was 70% based on the initial TFPA charged. Analysis of the material remaining in the cell indicated 87.5% conversion of TFPA; yield of HFC-338pcc based on TFPA converted was 80%.

Examples 21–24 were carried out in a manner similar to Example 20. Results are summarized in Table 2.

TABLE 2

| Ex. | Volume, ml Org. Liq. | Volume, ml $H_2O$ | mmoles TFPA | mmoles NaOH | Current (amp) | Coul.[a] | % HFC-338[b] |
|---|---|---|---|---|---|---|---|
| 21 | 40 | 40 | 80 | 40 | 4 | 15,000 | 75 |
| 22 | 40 | 40 | 332 | 160 | 4 | 60,000 | 83 |
| 23 | 26 | 54 | 129 | 10 | 2–4 | 24,000 | 79 |
| 24 | 50 | 50 | 303 | 150 | 4 | 30,000 | 49 |

[a] Coulombs
[b] Based on TFPA converted

EXAMPLE 25

Continuous Conversion of TFPA Methyl Esters to HFC-338pcc

A 250 ml flask was charged with methanol (50 ml), water (50 ml), and sodium hydroxide 12.4 g, 0.31 mole). Methyl 2,2,3,3-tetrafluoropropionate (48.0 g, 0.30 mole) was added dropwise to the solution over the course of 0.5 h and the mixture was then refluxed for 0.5 h. The resulting clear solution was poured into the electrolysis cell. The solution was cooled to 18° C. and electrolyzed at a current of 4 amps until 49,000 coulombs had been passed. During this time the temperature rose to 40° C. and the voltage increased from 12 to 16 v. During the electrolysis the concentration of $CHF_2CF_2CO_2-$ was maintained at a high level by adding the methyl ester continuously at a rate of 0.3 ml/min; a total of 46.8 g (0.292 mole) of ester were added to the cell over a pH range of 7.1 to 7.7. After 28,700 coulombs had been passed the concentration of $CHF_2CF_2CO_2-$ was allowed to decrease and the pH rose to about 8.4. Sodium bicarbonate precipitated in the cell during the course of the electrolysis.

The products in the dry ice trap were collected periodically. The following product was obtained:

| Product | mmoles |
|---|---|
| $CHF_2CHF_2$ | 2.5 |
| $CHF_2CF_2CHF_2$ | 1.9 |
| $CH_3OCHF_2$ | 0.7 |
| $CH_3OH$ | 35.5 |
| $CHF_2(CF_2)_2CHF_2$ | 154.5 |
| $CH_3OCF_2CHF_2$ | 3.8 |
| $CHF_2CF_2CO_2CH_3$ | 5.0 |

Analysis of the material remaining in the electrolysis cell indicated that the TFPA conversion was 82%. The yield of HFC-338pcc based on TFPA converted was 63%.

EXAMPLE 26

When the following organic liquids were used in place of methanol in experiments similar to Example 21, the following yields of HFC-338pcc were obtained:

| Organic Liquids | HFC-338 pcc, % yield |
|---|---|
| Methanol:acetonitrile (1:1) | 63 |
| Ethanol | 54 |
| t-Butanol | 34 |

-continued

| Organic Liquids | HFC-338 pcc, % yield |
|---|---|
| Ethylene Glycol | 14 |

EXAMPLE 27

Preparation of 1,1,2,2,3,3,4,4-Octafluorobutane (HFC-338pcc) by Kolbe Electrolysis of 2,2,3,3-Tetrafluoropropionic Acid (TFPA) in a Continuous Flow Cell Apparatus A flow electrolysis apparatus consisting of a DC power source, a plate and frame flow electrolysis cell used without a membrane (undivided MP cell manufactured by Electrocell AB, Taby, Sweden), a glass reservoir to contain the electrolyte, a pump to circulate the electrolyte from the reservoir to the cell, a reservoir of TFPA and pump to feed the TFPA to the reservoir, and a pH meter interlocked to the TFPA feed pump. The electrolysis cell was fitted with a planar 100 cm$^2$ stainless steel cathode and planar 100 cm$^2$ platinum foil anode. The electrolyte reservoir was fitted with an inlet for return of electrolyte and product from the cell, an outlet for electrolyte to be pumped to the cell, a TFPA inlet, and a water-cooled condenser connected to a dry ice trap.

A solution of TFPA (328.5 g, 2.25 mole) in 1:1 (by volume) methanol:water was neutralized with NaCH (90 g, 2.25 mole) and the resulting solution diluted to 0.75 L. This solution was charged to the electrolyte reservoir. The electrolyte was recirculated through the cell at a rate of 1.5 gallon/minute (5.7 L/min) and the temperature of the electrolyte was maintained at 40° C. by means of recirculating coolant through a cooling jacket on either side of the electrodes and through coils located inside the electrolyte reservoir. The TFPA electroylsis was performed at a current of 40 amp (current density=400 ma/cm$^2$, voltage=13.7–15.1 V). The electrolyte was maintained at pH=4 by continuous feed of pure TFPA to the reservoir by means of the metering pump interlocked to the pH electrode in the system. The liquid and vapor exiting the electrolysis cell disengaged in the reservoir and the product vapors passed through the water condenser and into the dry ice trap. Essentially all of the HFC-338pcc produced was condensed in the dry ice trap; some of the vapors (e.g., hydrogen, oxygen, tetrafluoroethylene and some 1,1,2,2-tetrafluoroethane) passed through the dry ice trap.

Under these conditions, passing 320,000 coulombs of charge through the cell resulted in the formation of the following products collected in the dry ice trap:

| Product | mmoles produced |
|---|---|
| CHF$_2$CHF$_2$ | 3.0 |
| CHF$_2$CF$_2$CHF$_2$ | 6.1 |
| CHF$_2$OCH$_3$ | 2.3 |
| Methanol | 409.5 |
| HFC-338 pcc | 1185.5 |
| CHF$_2$CF$_2$OCH$_3$ | 34.6 |
| CHF$_2$CF$_2$CO$_2$CH$_3$ | 1.8 |

During this time a total of 2.77 moles of TFPA were fed to the cell and the concentration of TFPA in the electrolyte remained essentially constant. The yield of HFC-338pcc based on TFPA converted was 86%.

What is claimed is:

1. Process comprising contacting and reacting a cyanide salt selected from the group consisting of MCN wherein M is an alkali metal having an atomic number greater than or equal to 11, Ca(CN)$_2$, Mg(CN)$_2$, and R$_4$NCN where R is C$_1$-C$_4$ alkyl; water and tetrafluoroethylene in the presence of an alcohol, wherein the alcohol is selected from the group consisting of ROH where R is C$_1$-C$_8$ alkyl, ethylene glycol, propylene glycol, 1,4-butanediol, and mixtures thereof.

2. Process according to claim 1 conducted at a temperature of about 15° to 125° C.

3. Process according to claim 2 conducted at a temperature of about 40° to 100° C.

4. Process according to claim 1 wherein the cyanide salt is selected from the group consisting of NaCN, KCN, and R$_4$NCN wherein R is C$_1$-C$_4$alkyl.

5. Process according to claim 4 wherein the cyanide salt is selected from the group consisting of NaCN and KCN.

6. Process according to claim 1 wherein the molar ratio of water to cyanide salt is about 2:1 to about 50:1.

7. Process according to claim 6 wherein the molar ratio of water to cyanide salt is about 4:1 to about 20:1.

8. Process according to claim 1 wherein the alcohol is ROH and R is C$_1$-C$_4$ alkyl.

9. Process according to claim 8 wherein the alcohol is methanol.

10. Process according to claim 1 wherein water comprises about 5% to about 95% by volume of the water and alcohol present.

11. Process according to claim 10 wherein water comprises about 10% to about 75% by volume of the water and alcohol present.

12. Process according to claim 11 wherein water comprises about 20% to about 60% by volume of the water and alcohol present.

13. Process according to claim 1 conducted at a pressure of about 15 psi (103 kPa) to about 1000 psi (6900 kPa).

14. Process according to claim 13 conducted at a pressure of about 50 psi (345 kPa) to about 300 psi (2070 kPa).

15. Process according to claim 1 wherein the process is carried out in the presence of water-miscible organic liquid selected from the group consisting of acetonitrile, propionitrile, dimethyl formamide, dimethyl acetamide, and tetrahydrofuran.

16. Process according to claim 1 wherein the 2,2,3,3-tetrafluoropropionate salt is obtained in a reaction mixture, said process further comprising freeing said reaction mixture of ammonia and alcohol, acidifying said reaction mixture by the addition of mineral acid to form as a result thereof 2,2,3,3-tetrafluoropropionic acid, and isolating said acid from the reaction mixture.

17. Process according to claim 1 wherein the 2,2,3,3-tetrafluoropropionate salt is obtained in a reaction mixture, said process further comprising freeing said reaction mixture of ammonia, acidifying said reaction mixture by the addition of mineral acid in the presence of a C$_1$-C$_4$ alcohol to form as a result thereof 2,2,3,3-tetrafluoropropionate ester, and isolating from the reaction mixture said ester, or its azeotrope with the corresponding C$_1$-C$_4$ alcohol, or a mixture thereof.

18. Process according to claim 17 wherein the ester is methyl or ethyl 2,2,3,3-tetrafluoropropionate and the alcohol is methanol or ethanol.

19. The composition comprising about 9 to about 60% by weight of a C$_1$-C$_4$ alkyl 2,2,3,3-tetrafluoropropionate ester and about 90 to about 40% by weight of the corresponding $C_1$-$C_4$ alcohol.

20. The composition according to claim 19 wherein the propionate ester is the methyl or ethyl ester and the alcohol is methanol or ethanol, respectively.

21. The azeotrope of methyl 2,2,3,3-tetrafluoropropionate and methanol boiling at about 63.0°–64.5° C. containing about 46–48% by weight of propionate ester and about 52–54% by weight of methanol.

* * * * *